(12) United States Patent
Paffrath

(10) Patent No.: US 6,363,565 B1
(45) Date of Patent: Apr. 2, 2002

(54) BRUSH ARRANGEMENT AND TOOTHBRUSH WITH BRUSH ARRANGEMENT

(75) Inventor: Dieter Paffrath, Seefeld (DE)

(73) Assignee: Braun GmbH (DE)

(*) Notice: Subject to any disclaimer, the term of this patent is extended or adjusted under 35 U.S.C. 154(b) by 0 days.

(21) Appl. No.: 09/658,584

(22) Filed: Sep. 8, 2000

Related U.S. Application Data

(63) Continuation of application No. PCT/EP00/00108, filed on Jan. 10, 2000.

(30) Foreign Application Priority Data

Jan. 12, 1999 (DE) ......................................... 199 00 765

(51) Int. Cl.[7] .............................. A46B 7/08; A46B 9/04; A61C 17/22; A61C 17/26

(52) U.S. Cl. ........................ 15/28; 15/22.1; 15/DIG. 5

(58) Field of Search ............................. 15/221, 23, 28, 15/DIG. 5; 300/21

(56) References Cited

U.S. PATENT DOCUMENTS

| | | | |
|---|---|---|---|
| 1,482,027 A | | 1/1924 | Ochse |
| 1,684,481 A | * | 9/1928 | Exley .............................. 15/28 |
| 2,044,863 A | | 6/1936 | Sticht |
| 4,020,522 A | * | 5/1977 | Behrend ........................ 15/28 |
| 4,570,282 A | | 2/1986 | Kaufman et al. |
| 4,729,142 A | | 3/1988 | Yoshioka |
| 4,739,532 A | | 4/1988 | Behrend |
| 4,776,054 A | | 10/1988 | Rauch |
| 4,892,698 A | * | 1/1990 | Weihrauch .................... 300/21 |
| 5,046,213 A | | 9/1991 | Curtis et al. |
| D329,946 S | | 10/1992 | Curtis et al. |

(List continued on next page.)

FOREIGN PATENT DOCUMENTS

| | | |
|---|---|---|
| CH | 676663 A5 | 2/1991 |
| DE | 889 135 | 7/1953 |
| DE | 2 208 031 | 9/1972 |
| DE | 24 33 925 | 2/1976 |
| DE | 30 49 563 A1 | 7/1982 |
| DE | 37 44 630 A1 | 7/1989 |
| DE | 42 01 873 C1 | 5/1993 |
| DE | 44 02 366 A1 | 6/1994 |
| DE | 44 44 243 A1 | 6/1996 |
| EP | 0 613 666 A1 | 9/1994 |
| EP | 0 765 642 A2 | 4/1997 |
| FR | 683 311 | 6/1930 |
| FR | 2 502 918 | 10/1982 |
| FR | 2 776 170 | 9/1999 |
| GB | 1 286 416 | 8/1972 |
| WO | WO 90/03162 | 4/1990 |
| WO | WO 99/23910 | 5/1999 |

OTHER PUBLICATIONS

International Search Report, International Application Serial No.: PCT/EP 00/00108 (No Date).
corresponding PCT Int'l. Appl. WO 00/41592, pub'd. Jul. 20, 2000, w/search report.

*Primary Examiner*—Terrence R. Till

(57) ABSTRACT

The invention is directed to a brush arrangement for use in a toothbrush having an electric drive mechanism for causing oscillation of the brush arrangement relative to a motion axis (43). It comprises a bristle carrier (41) and a plurality of upstanding bristles anchored to the bristle carrier and grouped in clusters (44, 45). The brush arrangement has bristles or bristle tufts (45) disposed in a spaced relationship to the motion axis (43) and inclined at an angle of inclination of about 6°, for example, in the direction of the motion axis. The brush arrangement is particularly suited for the cleansing of interproximal areas and for the removal of dental plaque, being suitable to particular advantage for utilization in connection with toothbrushes permitting both a rotary motion about the motion axis and a vibrating reciprocating motion in the direction of the motion axis.

81 Claims, 3 Drawing Sheets

U.S. PATENT DOCUMENTS

| | | |
|---|---|---|
| 5,177,826 A | 1/1993 | Vrignaud et al. |
| 5,467,495 A | 11/1995 | Boland et al. |
| 5,504,959 A | 4/1996 | Yukawa et al. |
| 5,590,438 A * | 1/1997 | Chen et al. ............... 15/191.1 |
| 5,709,233 A | 1/1998 | Boland et al. |
| 5,827,064 A | 10/1998 | Bock |
| 5,862,559 A | 1/1999 | Hunter |
| 5,974,615 A | 11/1999 | Schwarz-Harmann et al. |
| 6,016,587 A | 1/2000 | Savitt et al. |

* cited by examiner

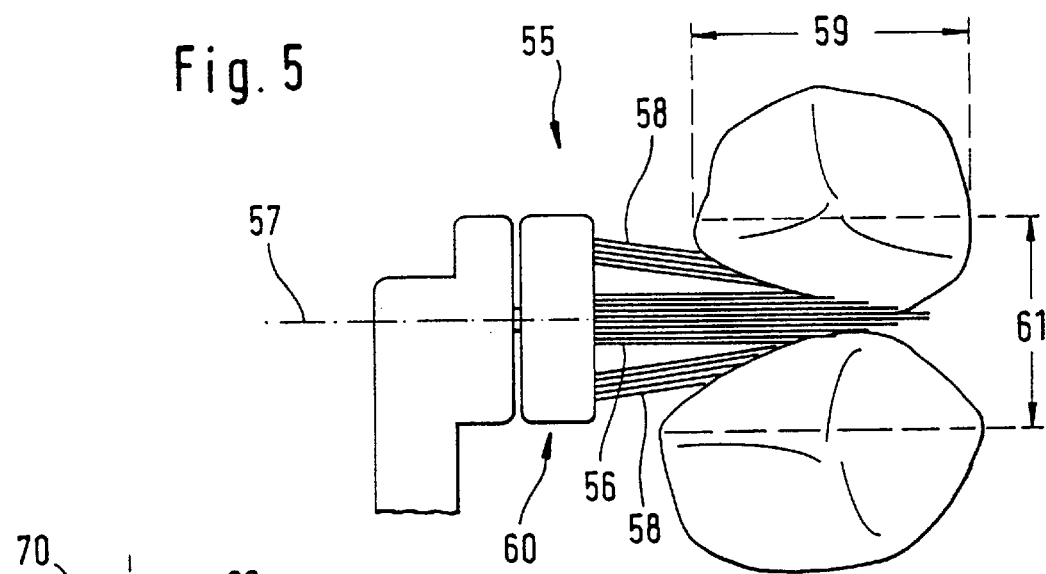
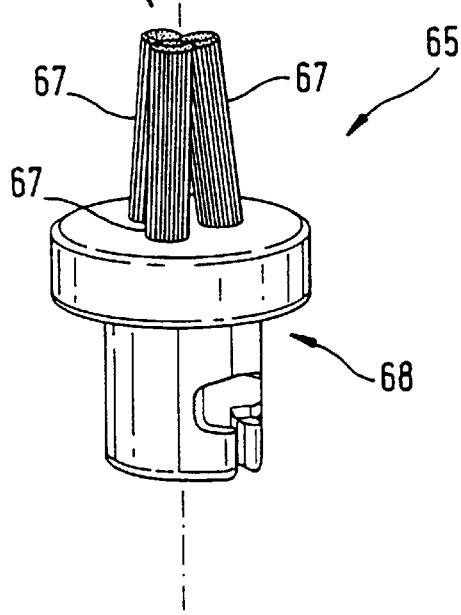
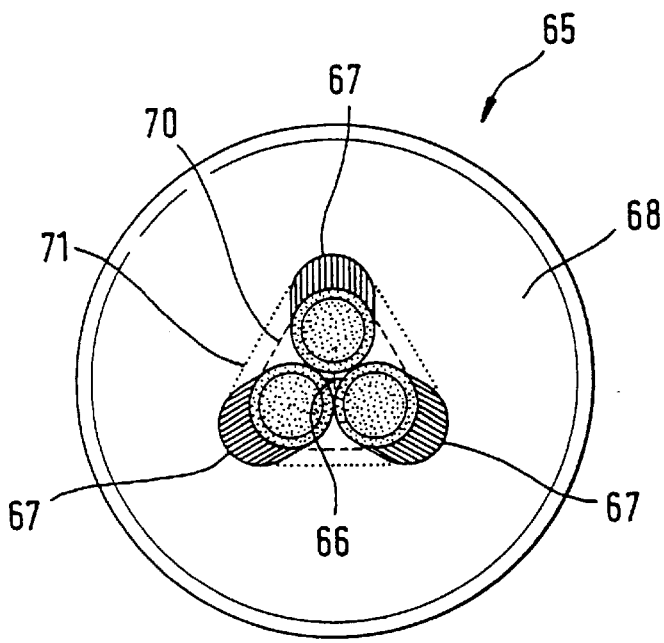

BRUSH ARRANGEMENT AND TOOTHBRUSH WITH BRUSH ARRANGEMENT

This is a continuation of International Application No. PCT/EP 00/00108, pending, with an International filing date of Jan. 10, 2000.

This invention relates to a brush arrangement.

Prior-art brush arrangements, also referred to as bristle or bristle tuft configurations, are intended for use in toothbrushes having a preferably electric drive mechanism for moving the brush arrangement relative to a motion axis of the brush arrangement. This may involve a preferably oscillating rotary motion about the motion axis and/or a preferably oscillating back-and-forth motion or vibratory motion in the direction of the motion axis. The brush arrangement comprises a bristle carrier and a plurality of upstanding bristles or bristle tufts anchored to the bristle carrier. The tree bristle ends define a working face also referred to as cleansing face because typically an appreciable part of the cleansing action is performed by the free bristle ends. Preferred fields of application of the present invention include the elimination of the film coating teeth, that is, dental plaque, in particular during the cleaning of interproximal spaces. Devices optimized for this purpose are frequently referred to as interproximal brushes.

For a long time only inadequate devices have been available for the cleansing and care of interproximal spaces unless performed by a dentist. Improvements have been sought by toothbrushes equipped with movably drivable brush arrangements. By way of example, DE 33 925 shows a toothbrush two hydrodynamically rotatable bristle carriers arranged side by side parallel to the axis. The slightly diverging bristles of the one bristle carrier form a working face in the form of a concave recess conforming to the convex outer shape of a molar, whilst the slightly diverging bristles of the other bristle carrier form a conical working face designed to enter into interproximal spaces. A similar suggestion is disclosed in U.S. Pat. No. 5,862,559. The toothbrush shown in this patent has a rotary brush arrangement with bristle tufts aligned parallel to the motion axis, the bristles thereof being suitably dimensioned in length so as to form overall an approximately conical working face designed to facilitate the cleaning of interproximal spaces. Another brush arrangement designed in particular for the cleaning of interproximal spaces is disclosed in EP 0 765 642. The brush arrangement which is adapted to rotate about a motion axis by means of an electric drive mechanism has its bristle tufts arranged in several concentric circles. The tufts of the outermost bristle circle are inclined in and in opposition to the direction of rotation in such fashion that they intersect a plane through the axis of rotation of the brush arrangement at an angle. This oblique position in the direction of movement is intended to improve the penetration of the bristles into the interproximal spaces during operation of the electric toothbrush, hence enhancing the dental cleansing effect.

It is an object of the present invention to provide a brush arrangement of the type referred to which affords ease of manufacture and provides further enhanced dental cleaning, in particular in the area of interproximal spaces, when used on a toothbrush having a drive mechanism for the brush arrangement.

To accomplish this object, the present invention proposes a brush arrangement with the features discussed herein below and a toothbrush with the features discussed herein below.

SUMMARY OF THE INVENTION

According to the present invention, provision is made for the brush arrangement to include bristles disposed in a spaced relationship to the motion axis, in particular eccentrically or concentrically, said bristles being inclined at an angle of inclination in the direction of the motion axis. Conveniently, the bristles are grouped in bristle clusters or bristle tufts which are aligned so that the center-of-gravity axes or axes of symmetry of the bristle tufts are inclined towards the motion axis. The inward inclination as disclosed in the invention has the effect that the free bristle ends of the inclined bristles tie closer to the motion axis than the bristle anchor points in the area of the bristle carrier. This enables a high bristle density advantageous for producing a good cleansing effect to be obtained in the area of the preferably rounded free ends, that is, in the area of the cleansing face or working face, while enabling, in the area of the fastening points e.g. anchor points on the bristle carrier, individual bristle tufts to be set at a sufficiently wide lateral distance to each other. Hence it is possible for each fastening points e.g. anchor point of a bristle tuft to be surrounded by sufficient bristle carrier material, to ensure its secure retention on the bristle carrier. When the anchor wire tufting technique is employed for manufacture, it is possible to set the hole mounts required to receive the bristle tufts at a sufficient lateral distance to each other so that tufting can be accomplished readily using conventional fixtures. In a preferred further aspect, for example, the inwardly oriented oblique position of bristles has the beneficial effect that the working or cleansing face is at least 20% smaller than the anchor area of the bristle carrier provided for tufting, with the size of the cleansing face preferably amounting to between about 50% and about 80% of the size of the anchor area. The term anchor area as used herein is understood to mean the surface area bounded by an envelope enclosing the bristles or bristle tufts in their base region close to the bristle carrier.

The angle of inclination or the oblique position may be selected so that the individual bristle tufts are able to bear against each other in the area of the working or cleansing face. This may significantly reduce bristle wear since it counteracts buckling.

Owing to the inwardly oriented oblique position or inclination of peripheral bristles or bristle tufts it is furthermore possible to produce a generally conical or frusto-conical array of bristles which facilitates introduction of the bristles into interproximal spaces. In contrast to conventional brush arrangements having bristles extending in substantially parallel alignment to each other, the oblique position has the added effect of causing the inclined bristles to respond more flexibly when subjected to axial loads, that is, loads parallel to the motion axis, so that the brush appears to exhibit a reduced axial stiffness. This may reduce or prevent the risk of gum injury as the brush arrangement is introduced into interproximal areas.

On a motion relative to the motion axis predetermined by the type of toothbrush, that is, in particular on a rotary oscillating motion about this axis, the oblique position has the beneficial effect that the individual bristles or bristle tufts of the brush arrangement conform themselves particularly well to the contours of the teeth bounding the interproximal space being worked and/or to the contour of the relevant gingival area, hence enabling the supra-gingival film (plaque) and the interproximal plaque to be removed more effectively. Owing to the invention arrangement of bristles or bristle tufts, a better cleansing operation can be accomplished of both punctiform (interproximal) and linear (gingival) areas of a person's teeth.

The cleansing effect may be supported, where applicable, by a pulsating or vibrating reciprocating motion essentially parallel to the motion axis. This poking motion may be of advantage also without a simultaneous rotary motion being performed. DE 196 27 752 (which corresponds to U.S. Pat. No. 5,994,615) discloses an electric toothbrush which is particularly suitable for utilization in connection with brush arrangements of the present invention and which permits both an oscillating rotary motion about the motion axis and an oscillating back-and-forth motion parallel to the motion axis.

In a preferred further aspect the angle of inclination is in the range of smaller than about 15°, in particular in the range of between about 4°, and about 8°. These relatively small angles of inclination are sufficient to produce the advantages of the invention, enabling, in particular at angles of inclination of up to about 8°, the brush arrangement to be manufactured using conventional fixtures for tufting with anchor wire. The brushes can be tufted with a 0° slope as for bristle tufts. Due to the oblique position limited to relatively small angles of inclination, it is furthermore possible to achieve rounding qualities higher than 90% for the free bristle ends.

In a further aspect provision is made for the brush arrangement to have at least one, preferably precisely one ring of bristles in which the bristles are arranged in an essentially circular array around the motion axis and are inclined in the direction of the motion axis in the manner described. Conveniently, the bristle ring arranged preferably concentrically with the motion axis is formed by several, in particular three, bristle tufts equally spaced apart circumferentially on the bristle carrier. Such a peripheral bristle ring provides the described frusto-conical outer contour of the bristle arrangement. The bristle tufts may be arranged symmetrically so that the axis of symmetry of the bristles or tufts coincides with the motion axis of the brush arrangement. As a result a uniform cleansing action is achievable on rotation about the motion axis and/or vibration along the motion axis.

A further feature is characterized in that the brush arrangement includes a center tuft of bristles arranged essentially concentrically with the motion axis and provided preferably in addition to a bristle ring surrounding the center tuft. This enables a variety of advantageous configurations to be implemented in which the properties of the brush arrangement in the center region, that is, in the region of the motion axis, differ from the properties in the surrounding peripheral area.

In particular provision may be made for the free ends of bristles in the area of the motion axis to protrude beyond the free ends of peripheral bristles, for example, by an amount of between about 0.5 mm and about 1.5 mm. This makes the center bristles the preferred choice for the cleansing of interproximal spaces, which operation is supported by a poking reciprocal motion along the motion axis and/or, where applicable, an oscillating rotary motion. The recessed, radially outer peripheral bristles may be used for working dental and gingival surfaces adjoining the interproximal spaces.

Hence a substantially convex, in particular conical or pyramidal working face may be implemented which may also be graduated. To increase the effective bristle length without incurring a reduction in brush stiffness in axial direction, provision may also be made for the brush carrier to have an elevation in the area of the motion axis, which is dimensioned such that the bristles in the area of the motion axis may be anchored above the level of peripheral bristles. For example, a central elevated platform of a height of between 1 mm and 2 mm may be provided on an otherwise plane, for example, disk-shaped bristle carrier section. With this construction, an essentially like free length of all the bristles of the array is achievable, while yet the bristles in the center area protrude beyond those on the periphery. Suitable bristle lengths, measured above the bristle carrier, Lie in the range from about 6.5 mm to about 8.5 mm, in particular at about 7.5 mm.

As an alternative or addition to the features relating to the bristle length and/or the shape of the working face, provision may also be made for the center bristles, that is, the bristles in the area of the motion axis, to be of greater hardness than the peripheral, eccentric bristles. The term hardness as used herein is understood to mean primarily the hardness perceivable by the user which, among other factors, is influenceable by the axial brush stiffness of the bristle material and/or the oblique position or inclination of bristles. In a preferred embodiment, the hardness of the bristles in the area of the motion axis is determined by a bristle strength of about 7±2 mil, and/or the hardness of eccentric bristles is determined by a bristle strength of about 6±2 mil. The dimension mil which indicates the bristle diameter corresponds to one thousandth of an inch equaling 0.0254 mm. Generally bristle diameters in the range of between about 4.5 to about 8 mil have proven in practice. In particular for reasons of hygiene and durability bristles formed from a plastics material are the preferred choice, particularly from PA 6.12 type nylon. However, it is also possible to fabricate part or all of the bristles from natural fiber.

The preferred embodiments of brush arrangements described in connection with the drawings are essentially configured so as to be symmetrical to the motion axis, the embodiment providing a center tuft having its center-of-gravity axis or axis of symmetry coincident with the motion axis. To enhance the cleaning action in combination with an oscillating motion of the brush arrangement (rotary and/or vibratory), provision may also be made for the axis of symmetry of the center tuft and/or the entire brush arrangement to be given a slight slope, for example, at an angle of inclination of the order of magnitude of between 2° and 6°, in particular about 4°, with respect to the motion axis. As an alternative or addition, it is also possible to provide for a lateral offset of the axis of symmetry of the entire brush arrangement and/or of only the center tuft with respect to the motion axis, for example, by about 0.5 to about 1 mm. For example, on a rotation about the motion axis, an oscillating transverse motion which is superposed upon the rotary motion results in a direction transverse to the motion axis, which may contribute to supporting the cleansing effect.

The present invention further relates to a toothbrush which is of great advantage particularly for the cleaning of interproximal spaces and the removal of plaque. It comprises a movably drivable brush arrangement including a bristle carrier and a plurality of upstanding bristles anchored to the bristle carrier, and a preferably electric drive mechanism for moving the brush arrangement relative to a motion axis. By using brush arrangements according to the present invention, such a toothbrush may be upgraded in simple manner to a dental care device which is particularly effective for the cleansing of interproximal spaces and/or the removal of dental plaque. Conveniently, the brush arrangement is associated with a separate, exchangeable brush section on attachable to a handle section of the toothbrush as by plugging it on. A preferred embodiment of a toothbrush which enables the brush arrangement to oscillate about the motion axis in a rotating motion and to oscillate along the motion axis in a reciprocating motion is disclosed in DE 196 27 752 (which corresponds to U.S. Pat. No. 5,974,615 whose features relating to the toothbrush and the brush section shall be deemed to be incorporated by reference herein and to be a part hereof.

The features described and further features of the present invention will also become apparent, from the subsequent description of a preferred embodiment taken in conjunction with the claims and the accompanying drawings. It will be understood that the individual features may be implemented each for itself or in combination with several other features.

BRIEF DESCRIPTION OF THE DRAWINGS

FIG. 5 is a schematic view showing the use of another embodiment of a bristle array of the present invention for cleaning an interproximal space, the brush arrangement comprising one center tuft having long bristles and peripheral tufts having short bristles, with the bristle length increasing progressively from the outside to the inside;

FIG. 6 is an oblique perspective view of another embodiment of a brush arrangement of the present invention, comprising three tufts inclined towards the center axis of the brush arrangement and absent a center tuft; and FIG. 7 is a top plan view of the brush arrangement of FIG. 6.

DETAILED DESCRIPTION OF PREFERRED EMBODIMENTS

Figure 1:
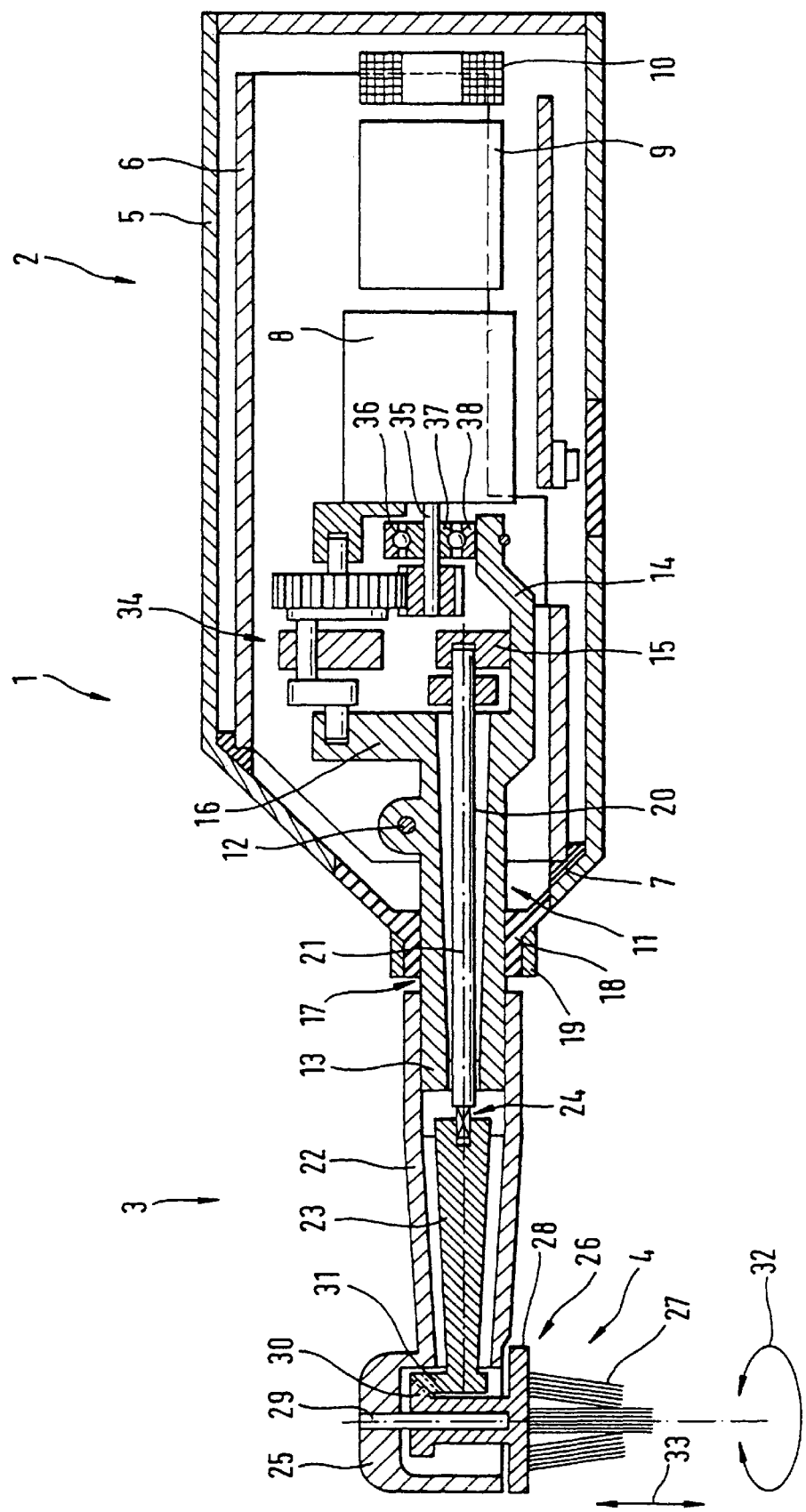
FIG. 1 is a schematic illustration of an embodiment of an electric toothbrush showing a first embodiment of a brush arrangement of the present invention.

FIG. 1 shows a preferred embodiment of an electric toothbrush 1 provided for cleaning a user's teeth, in particular for removing plaque from the tooth surfaces and for cleansing interproximal spaces. The toothbrush has a handle section 2 of an approximately cylindrical, elongated shape of a diameter such as to enable a user to hold the toothbrush securely by its handle section 2. Attachable to the forward end of the handle section 2 is a brush section 3 which is equally of an essentially cylindrical, elongated shape, with the diameter of the brush section 3 being smaller than that of the handle section to enable the brush section 3 to be introduced into the user's oral cavity. Provided at the free end of the brush section is a movably drivable brush arrangement 4 comprising plurality of bristles for cleaning teeth, gingiva and interproximal spaces.

The handle section 2 has a housing 5 in which a chassis 6 is received. The chassis 6 possesses an elongated, partly cylindrical form and extends nearly over the entire length of the housing 5. At its end close to the brush section 3 the chassis is elastically held in the housing 5 by cushions 7 made of a plastics material or rubber or equivalent.

Mounted on the chassis 6 are an electric motor 8, a storage battery 9 and further electronic components as, for example, a charging coil 10 and the like. The components identified are preferably arranged one behind the other in the longitudinal direction of the handle section 2.

In the area of the handle section 2 close to the brush section 3, provision is made for a rocker 11 which is pivotal about an axis 12. Part of the rocker 11 extends forwardly out of the handle section 2. The rocker comprises a tube 13, a cantilever 14 and two support arms 15, 16. Projecting from the handle section 2, the tube 13 of the rocker 11 is passed through an opening 17 at the end of the handle section 2 close to the brush section 3. Between the tube 13 and the housing 5 of the handle section 2 is an annular diaphragm 18 formed from a plastics material or rubber or equivalent, with which the tube 13 of the rocker 11 is elastically guided out of the handle section 2. A clamp 19 embracing the diaphragm 18 in annular fashion serves to hold and secure and seal the tube 13 in the housing 5 of the handle section 2.

At least that portion of the tube 13 that extends out of the handle section 2 possesses a cross-sectional shape whose outer diameter is contoured. The brush section 3 is adapted to be plugged onto this projecting section of the tube 13. The brush section 3 has at least at its end close to the handle section 2 a cross sectional shape with an inner diameter having a contour corresponding to the contour of the outer diameter of the tube 13. The associated contours are configured such that the brush section 3 can be attached to the handle section 2 in only one angular position. For example, the contour may be of a stellate or triangular configuration or the like.

With the brush section 3 plugged onto the tube 13 of the rocker 11, the brush section 3 forms a further component of the rocker 11, being hence pivotal about the axis 12.

Received in the tube 13 of the rocker 11 is a shaft 20 mounted for rotation on the free end of the tube 13 projecting from the handle section 2 at one end and in the support arm 15 at the other end. The shaft 20 extends approximately in the longitudinal direction of the handle section 2 and the brush section 3, defining an axis 21. The shaft 20, which is a further component of the rocker 11, protrudes from the tube 13 and has at its free end there a cross-sectional shape with a contoured outer diameter. The axis 12 of the rocker 11 and the axis 21 of the shaft 20 are in an approximately transverse alignment to each other.

The brush section 3 is attachable to the tube 13 of the rocker 11. The brush section 3 has a carrier tube 22 in which a brush shaft 23 is mounted for rotation. With the brush section 3 attached, the brush shaft 23 is arranged concentrically with the axis 21 and has a recess 24 at its end close to the handle section 2. The recess 24 has an inner diameter with a contour corresponding to the contour of the outer diameter of the shaft 20 projecting from the tube 13. The associated contours are configured so that in a particular angular position the shaft 20 is insertable into the recess 24, thereby forming a non-rotative connection therewith.

A shell 25 accommodating the brush arrangement 4 is held at the free end of the carrier tube 22 and hence at the free end of the brush section 3. The brush arrangement 4 comprises a bristle carrier 26 to which a plurality of bristles 27 are secured which project from the bristle carrier. The bristle carrier 26 has a disk-shaped section 28 to which the bristles 27 are anchored, and is mounted for rotation about an axis 29. The axis 29 extends through the center of the disk-shaped section 28 and is arranged to be approximately transverse to the axis 21 of the shaft 20 and likewise approximately transverse to the axis 12 of the rocker 11. Via two meshing bevel gear segments 30, 31, an alternating or oscillating rotary motion of the brush shaft 23 about the axis 21 may be translated into an alternating or oscillating rotary motion of the bristle carrier 26 about the axis 29. The axis 29 is hence a motion axis of the bristle carrier, serving as axis of rotation among other functions.

With the drive mechanism 8 activated, the bristle carrier 26 describes an alternating rotary motion (arrow 32) covering an angle-of-rotation range which may be between about ±15° and about ±40°. Hence the total travel may amount to between about 30° and about 80°. Preferably, the range of the angle of rotation is about ±30°, and the total travel is hence about 60°. Smaller angles of rotation and larger ones of up to about ±90° are also possible. Advantageously, the frequency of the alternating rotary motion (arrow 32) of the bristle carrier may be between about 50 Hz and about 80 Hz, in particular at about 63 Hz.

The alternating rotary motion of the brush arrangement 4 about the axis of rotation 29 is produced by the electric motor drive mechanism 8 which is in rotary driving connection with the shaft 20 by means of a suitable gear arrangement 34. For a more detailed description of the gear arrangement 34, reference is made to DE 196 27 752 (which corresponds to U.S. Pat. No. 5,974,615) whose contents shall be deemed to be part of this description by reference. The coupling between motor 8 and rocker 11 which is not described here in greater detail is designed so that at the same time a vibratory motion of the entire rocker 11 about its pivot axis 12 is produced. To accomplish this, a ball bearing 36 having an eccentric inner race 37 and a concentric outer race 38 is mounted on the motor shaft 35 of the motor 8, the outer race being fastened to the cantilever 14 of the rocker 11 support arm. Considering that the plugged-on brush section 3 represents part of the rocker 11, also the brush arrangement 4 is set in a vibratory pivotal motion about the axis 12. Because the axis 12 extends in a direction approximately transverse to the motion axis 29, the brush arrangement performs accordingly a reciprocating back-and-forth motion (arrow 33) in a direction about parallel to the axis 29. The motion axis 29 thus also represents an axis of reciprocation of the brush arrangement.

The reciprocating motion causes the bristles 27 of the brush arrangement to perform a poking movement substantially parallel, or at an acute angle, to the bristle direction. The stroke length of the reciprocating back-and forth motion 33 may advantageously lie in a range from about ±0.02 mm to about ±0.2 mm, amounting to a total travel of between about 0.04 and about 0.4 mm. Preferably the stroke length of the reciprocating motion 33 is about 0.14 mm, corresponding to a total travel of about 0.28 mm. The frequency of the reciprocating back-and-forth motion may be between about 130 Hz and about 200 Hz, in particular at about 164 Hz. Hence the frequency of the reciprocating motion 33 is significantly higher than that of the rotary motion 32.

Figure 2:
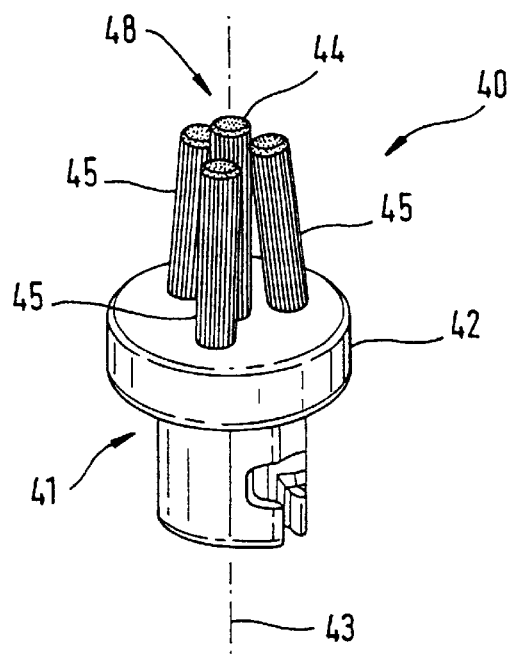
FIG. 2 is an oblique perspective view of a preferred embodiment of a brush arrangement comprising a center tuft and three peripheral tufts arranged at an inclination to the center tuft.
Figure 3:
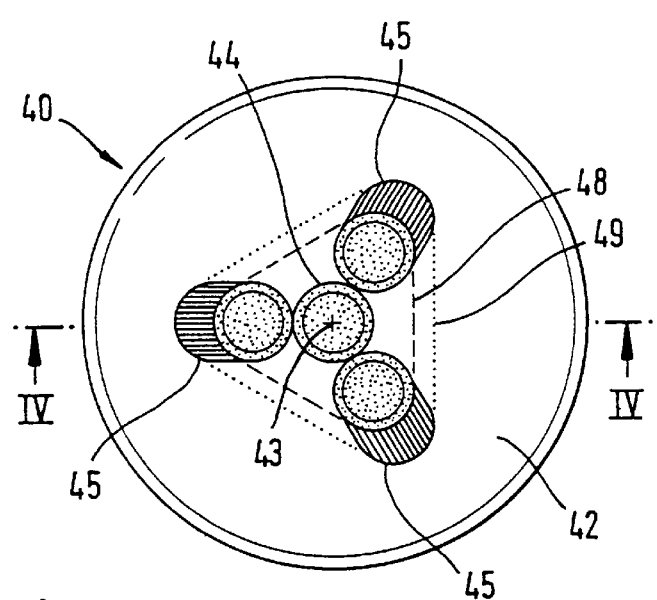
FIG. 3 is a top plan view of the brush arrangement of FIG. 2.
Figure 4:
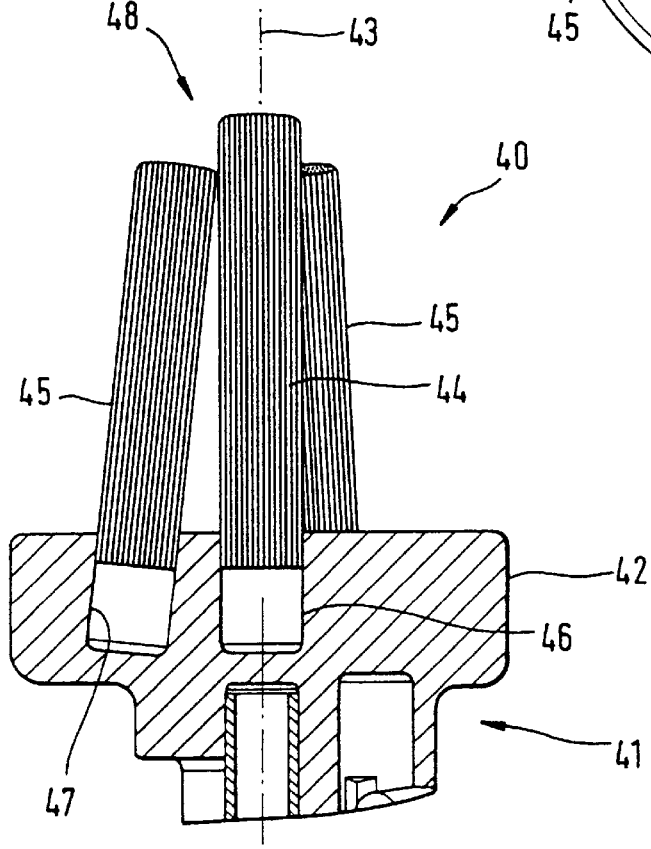
FIG. 4 is a sectional view of the brush arrangement of FIGS. 2 and 3, taken along the line IV—IV of FIG. 3.

Preferred embodiments of brush arrangement will be described in more detail in the following. The embodiment of a brush arrangement 40 illustrated in FIGS. 2 to 4 is substantially identical to the brush arrangement 4 of FIG. 1. The bristle carrier 41 fabricated from a plastics material has a disk-shaped section 42 adjoined by an integrally formed coupling section of reduced diameter which serves the function of coupling the brush arrangement 40 to a brush section and transmitting the force for effecting rotation of the brush arrangement about a motion axis 43. Fixedly anchored in the bristle carrier 41 are four bristle tufts, including one center tuft 44 arranged coaxially with the axis 43 and three eccentric bristle tufts 45 disposed around the center tuft 45 in a circular ring and being each inclined in the direction of the center axis 43 by like angles of inclination of about 5° to 6°.

The tufts 44, 45 are anchored in the disk section 42 using the conventional anchor wire tufting technique. For this purpose, the bristle carrier 41 has in the area of the disk-shaped section 42 four correspondingly aligned blind-end bores 46, 47 of like diameter in the range from 1.4 to 1.8 mm, in particular about 1.6 mm, including a center blind-end bore 46 coaxial with the motion axis 43, and three radially outer tying bores 47 which are circumferentially spaced apart by 120° and have their bore axes inwardly inclined by about 6° in the direction of the center axis 43. The lateral distance between the bores which also may be of different diameter amounts to about 50 to 80% of the bore diameter, enabling the minimum distance of about 0.7 mm advantageous for anchor wire tufting to be maintained with ease.

Each tuft 44, 45 contains exclusively plastic bristles formed preferably from PA 6.12 type nylon. The bristles of the center tuft 44 which appear white or colorless have a mean bristle strength or a mean bristle diameter of about 0.18 mm, the mean number of bristles per tuft amounting to about 52±4 in the embodiment with a blind-end bore diameter of about 1.6 mm. With a mean bristle diameter of 0.15 mm, the bristles of the peripheral tufts 45 are thinner and accordingly less rigid than the bristles of the center tuft. The mean bristle number here is about 64±4 bristles per tuft. For better distinction, these bristles are colored, for example, green. The bristle length, measured from the disk section 42, is about 7.5±1 mm for the peripheral tufts, while the bristles of the center tuft 44 are about 1.0±0.5 mm longer. This results in the area of the rounded free bristle ends in a working or cleansing face 48 which is formed in the manner of a triangular step pyramid with a center area which is raised relative to the peripheral areas.

Owing to the oblique position of the peripheral tufts 45, with a mean envelope diameter of about 3.15 mm the working face 48 shown in FIG. 3 in broken lines is appreciably smaller than the anchor area 49. The anchor area is bounded by an envelope (shown as a dotted line in FIG. 3) connecting the bristle tufts in their base area on the outsides. Accordingly, the oblique position of the peripheral tufts enables the bristle hole mounts 46, 47 to be located at a sufficient relative distance to render tufting an easy matter using the anchor wire tufting method on the one hand, while on the other hand making it possible to obtain a relatively small working face by comparison with the anchor area, which permits directionalized working, and in particular in connection with the oblique position of the peripheral tufts, ready penetration of bristles into interproximal spaces.

The oblique position of the peripheral tufts has the added effect of reducing the axial bristle stiffness perceived by the user, meaning practically a resistance to deformation by compression in the direction parallel to the axis 43, by comparison with the bristles of the center tuft. This thus also diminishes the risk of gum injury as the bristles are forced into interproximal spaces. Furthermore the tufts contacting each other partially in the area of the free bristle ends bear against each other, with in particular the three oblique tufts 45 supporting the center tuft 44. This contributes Lo reducing brush wear significantly.

FIG. 5 shows schematically another embodiment of a brush arrangement 55 comprising equally one center tuft 56 and three eccentric tufts 58 disposed in a ring around the center tuft and inclined at an angle of inclination of about 8° relative to the motion axis 57. As can be seen, the maximum free length of the center bristles corresponds at most to about the maximum depth 59 of the interproximal space in horizontal direction, and the diameter of the disk-shaped section of the bristle carrier 60 is about of the order of magnitude of a lateral distance 61 between the front edges of two adjacent teeth. As a result, the bristles introduce themselves into the interproximal space in a self-centering effect. Unlike the embodiment shown in FIGS. 2 to 4, the bristles are provided with a chamfer for enhanced guided entry of the bristles in the interproximal space, said chamfer being executed so that the bristles increase in length from outside to inside, producing overall an approximately conical working face. Those bristles which do not fit into the interproximal space because of its tightness are able to flex in part, being thus available for cleaning the region immediately adjacent to the interproximal space. The bristles serving this function are primarily the peripheral bristles which, as mentioned, are preferably softer than the bristles of the center tuft. Because the outer bristle ring has tufts directed inwardly at an angle of inclination, particularly effective introduction into the interproximal space is possible with the bristles rotating.

With a view to using the toothbrush as an interproximal brush, the embodiments hitherto described afford in particular the following advantages: Owing to the special arrangement (outer chamfer), shaping and size of the bristles these find their way into the interproximal spaces practically on their own, without this requiring particular dexterity, because the bristles center themselves automatically in the interproximal space as a result of the rotation about the motion axis. This space is cleansed optimally because a smaller or greater number of bristles can be forced into the interproximal space, depending on the pressure applied manually, thereby ensuring a largely complete removal of plaque. As set forth in connection with FIG. 5, the bristles may be adapted in length to the width of the interproximal space so that they are able to pass through the full interproximal space. The fact that under circumstances part of the bristles is flexed outwardly during rotation, in particular the eccentric bristles in the peripheral area, presents no disadvantage because it has the concomitant effect of cleaning at the same time also the direct neighborhood of the interproximal space. In addition, cleaning of existing periodontal pockets is also possible in which food debris and bacteria are known to accumulate. Owing to the generally frusto-conical or conical outer contour of preferred brush arrangements, the bristles are able to conform themselves to different dentitions well. Wide spaces are cleaned by introducing the bristles into the space between teeth a correspondingly deeper amount, while narrow spaces may be cleaned solely by the long center bristles. The configuration which, by virtue of its arrangement (oblique position) and/or material properties (bristle diameter, for example) affords ease of implementation and is constructed so that outer, peripheral bristles are softer than inner, center bristles, reliably prevents the possibility of gum injury and may be used for massaging the gums.

FIGS. 6 and 7 show another embodiment of a brush arrangement 65 of the present invention which differs from the embodiment of FIGS. 2 to 4 essentially in that it has no center tuft and the outer bristle ring is of reduced diameter. Provision is made for only three peripheral tufts 67 arranged in the manner of a ring around the axis of symmetry or motion axis 66 of the brush arrangement. The tufts are inclined at an angle of inclination of about 6° in the direction of the axis of symmetry 66, causing the tufts to abut each other in the area of their free bristle ends, while in the anchor area close to the bristle carrier 68 they are spaced at a lateral relative distance of about 0.7 mm. The bristles of the tufts 67 are identical to the bristles of the peripheral tufts 45 of the embodiment of FIGS. 1 to 4 as regards bristle length, strength and material. In contrast to this embodiment, the hole mounts for receiving the tufts are in closer vicinity to each other and there is no center hole mount.

Owing to their oblique position the three tufts 67 are flexible. By comparison with conventional tufts of like material yet not sloping, the axial brush stiffness is however reduced, and the dimension of the substantially flat working face or cleansing face 70 in the area of the free bristle ends is minimized to a value of about 4.5 to 6 mm$^2$ on account of the abutment of the tufts. By contrast, with straight bristles, that is, bristles extending parallel to the axis 66, the surface area covered by the working face 70 would correspond to the anchor area 71 whose mean diameter is about 3.8 mm. Being sloping, the individual tufts bear against each other, which reduces in particular brush wear. The slim, in particular approximately frusto-conical shape of the complete brush arrangement and the flexible individual tufts enable in advantageous manner both the cleaning of tooth surfaces and the interproximal penetration as is desirable for interproximal brushes.

The embodiments shown are implemented using the anchor wire tufting method including the steps of providing first the corresponding boreholes for mounting the bristle tufts and then tufting and securing the tufts in the mounts. Because preferred angles of inclination of, for example, 6° are relatively small, no complex changes need be made in principle on conventional jigs and fixtures for manufacturing tho boreholes. The possibility also exists to manufacture invention brush arrangements by injection-molding suitable material around the tufts and connecting them with an injection-molded bristle carrier. It will be understood, of course, that more than three or four individual tufts may be inserted, such as five, six, seven or eight. An embodiment not shown has only two tufts. In this case the axis of symmetry of the bore arrangement may be transverse to the axis of the mouthpiece. Preferably the ends of all bristles or tufts are rounded which may be accomplished, for example, by grinding using conventional drums or disks provided with abrasive paper or coated with diamond powder. From the point of view of manufacturing engineering it is advantageous for the brush arrangements shown in FIGS. 1 to 5 to tuft and round first the short bristles, tufting and rounding the long tuft in a subsequent operation. In the embodiment of FIG. 5 the working face may be shaped to its conical configuration by suitably grinding it subsequent to the tufting of all bores.

Experiments have shown that the embodiment of FIGS. 1 to 4 and also the embodiment of FIG. 5 permits enhanced interproximal penetration by comparison with the embodiment of FIGS. 6 and 7. A slightly diminished cleansing action in the gingival area is possibly attributable to the repelling effect of the center tuft. If a particularly effective cleaning action is desired in this region, an embodiment similar or identical to the one of FIGS. 6 and 7 may be employed to advantage. In an overall view taking into account the cleansing ability in both the interproximal area and the gingival area, all embodiments described reveal essentially comparable cleaning results which are significantly superior to those of conventional brush arrangements for interproximal brushes.

What is claimed is:
1. An interproximal brush arrangement for use in a toothbrush having a drive mechanism for causing movement of the brush arrangement relative to a motion axis of the brush arrangement, said brush arrangement comprising
   a bristle carrier,
   a plurality of bristle tufts each comprising a plurality of bristles,
   each said tuft having a proximal end secured to the bristle carrier, a distal free end remote from its proximal end, and a median axis extending between its proximal and free ends, at least a first of said bristle tufts extending substantially parallel the motion axis, and a second group of said plurality of bristle tufts being disposed about the first bristle tuft in spaced relation to the motion axis and having each respective median axis inclined in the direction of the first bristle tuft.

2. The interproximal brush as claimed in claim 1, wherein the first bristle tuft is coincident with the motion axis.

3. The interproximal brush as claimed in claim 1, wherein distal portions of said second group of said plurality of bristle tufts abut the first bristle tuft.

4. The interproximal brush as claimed in claim 1, wherein said second group of tufts have median axes intersecting the motion axis.

5. The interproximal brush as claimed in claim 1, wherein said at least first bristle tuft is a single tuft.

6. The interproximal brush as claimed in claim 1, wherein said second group of tufts comprises at least three tufts.

7. The interproximal brush arrangement as claimed in claim 1, wherein the motion axis is a rotational axis about which the bristle carrier undergoes rotary motion.

8. The interproximal brush arrangement as claimed in claim 1, wherein the distal ends are arranged within an imaginary boundary circumferentially enclosing the tufts adjacent the free ends, said boundary having in a projection onto a plane transverse the motion axis a major dimension less than a lateral distance between outside edges of two adjacent teeth.

9. The interproximal brush arrangement as claimed in claim 8, wherein the major dimension is approximately a diameter not exceeding about 3.15 mm.

10. The interproximal brush arrangement as claimed in claim 1, further including brush supporting structure supporting the motion axis of the brush arrangement, the brush arrangement being movable relative the supporting structure, and the bristle tuft distal ends extending substantially further outward, in a direction extending from the bristle carrier towards the distal ends, than portions of the brush supporting structure.

11. The interproximal brush arrangement as claimed in claim 1, wherein the tufts are inclined at an angle of less than about 15°.

12. The interproximal brush arrangement as claimed in claim 1, wherein the tuft distal ends form a working face having an area bounded by an imaginary distal envelope enclosing the distal ends, wherein an anchor area along the bristle carrier is bounded by a base envelope enclosing the bristle tufts near their proximal ends, and wherein the working face area is less than the anchor area.

13. The interproximal brush arrangement as claimed in claim 1, wherein the tuft distal ends form a working face having an area bounded by an imaginary distal envelope enclosing the distal ends, the working face area being between about 3 mm$^2$ and about 8 mm$^2$.

14. The interproximal brush arrangement as claimed in claim 1, wherein the free ends of bristles radially more adjacent the motion axis protrude beyond the free ends of bristles which are radially more remote from the motion axis.

15. The interproximal brush arrangement as claimed in claim 1, wherein bristles of the first tuft have distal free ends that protrude beyond the free ends of the second group of bristle tufts.

16. The interproximal brush arrangement as claimed in claim 1, wherein the bristles radially more adjacent the motion axis are of greater hardness than the bristles which are radially more remote from the motion axis.

17. The interproximal brush arrangement as claimed in claim 1, wherein the bristle carrier defines hole mounts for receiving bristle tufts, and that the bristle tuft proximal ends are secured in the bristle carrier holes using anchor wire tufting.

18. The interproximal brush arrangement as claimed in claim 1, wherein the bristle tuft proximal ends are secured in the bristle carrier by injection molding.

19. The interproximal brush arrangement as claimed in claim 1 in combination with a toothbrush having an electric drive mechanism for moving the brush arrangement relative to the motion axis.

20. The interproximal brush arrangement as claimed in claim 1 in combination with a brush support section having a shaft adapted to be driven in rotation by the toothbrush and being in driving connection with the brush arrangement for causing movement of the brush arrangement relative the motion axis, the combination brush support section with the brush arrangement being removably attachable to the toothbrush.

21. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft comprising a plurality of bristles, each bristle tuft having a proximal end secured to the bristle carrier and a distal free end remote therefrom, wherein, near the proximal ends, centers of the bristle tufts are spaced from one another, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation.

22. The brush arrangement as claimed in claim 21, wherein the bristle tufts are arranged eccentric or concentric relative the motion axis.

23. The brush arrangement as claimed in claim 21, wherein the tufts are inclined at an angle of less than about 15°.

24. The brush arrangement as claimed in claim 23, wherein the angle is in the range of between about 4° and about 8°.

25. The brush arrangement as claimed in claim 21, wherein the tuft distal ends form a working face having an area bounded by an imaginary distal envelope enclosing the distal ends, the working face area being between about 3 mm$^2$ and about 8 mm$^2$.

26. The brush arrangement as claimed in claim 25, wherein the working face area is between about 4 mm$^2$ and about 6 mm$^2$.

27. The brush arrangement as claimed in claim 21, further having bristles which are radially more adjacent the motion axis whose distal free ends protrude beyond the free ends of bristles which are radially more remote from the motion axis.

28. The brush arrangement as claimed in claim 27, wherein the bristles more adjacent the motion axis protrude by an amount of between about 0.5 mm and about 1.5 mm.

29. The brush arrangement as claimed in claim 21, wherein the bristle carrier has an elevation in a region adjacent the motion axis which is dimensioned such that bristles adjacent the motion axis are secured above a level of bristles spaced further the motion axis.

30. The brush arrangement as claimed in claim 29, wherein said elevation is of a height preferably between about 1 mm and about 2 mm.

31. The brush arrangement as claimed in claim 21, wherein the plurality of inclined bristle tufts includes at least three tufts arranged around the motion axis and having their proximal ends intersecting an approximate circular ring.

32. The brush arrangement as claimed in claim 21, wherein the bristles have a free length of between about 6.5 mm and about 8.5 mm.

33. The brush arrangement as claimed in claim 32, wherein the bristles have a free length of about 7.5 mm.

34. The brush arrangement as claimed in claim 21, wherein the tuft distal ends collectively form a convex working face.

35. The brush arrangement as claimed in claim 34, wherein the convex working face is generally conical or pyramidal or stepped.

36. The brush arrangement as claimed in claim 21 in combination with a toothbrush having an electric drive mechanism for moving the brush arrangement relative to the motion axis.

37. The brush arrangement as claimed in claim 21, wherein the tufts have longitudinal axes extending between their proximal and distal ends and the longitudinal axes are inclined intersecting the motion axis.

38. The brush arrangement as claimed in claim 21, wherein all tufts on the bristle carrier are inclined.

39. The brush arrangement as claimed in claim 21, wherein the motion axis is a rotational axis about which the bristle carrier undergoes rotary motion.

40. The interproximal brush arrangement as claimed in claim 21, wherein each said tuft of bristles has its proximal end mounted in respective separate apertures in the bristle carrier.

41. The interproximal brush arrangement as claimed in claim 21, wherein each said tuft of bristles has a median axis extending between the proximal and distal ends, each said bristle tuft comprising a plurality of filaments arranged on opposite sides of the median axis.

42. The brush arrangement as claimed in claim 21 in combination with a brush support section defining a cavity therein and having a shaft rotationally disposed therein and adapted to be driven in rotation by the toothbrush and being in driving connection with the brush arrangement for causing movement of the brush arrangement relative the motion axis, the bristle carrier being moveable relative the brush support section, the combination brush support section with brush arrangement being removably attachable to the toothbrush.

43. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and wherein the tuft distal ends form a working face having an area bounded by an imaginary distal envelope enclosing the distal ends, wherein an anchor area along the bristle carrier is bounded by a base envelope enclosing the bristle tufts near their proximal ends, and wherein the working face area is less than the anchor area.

44. The brush arrangement as claimed in claim 43, wherein the working face area is less than about 80% of the anchor area.

45. The brush arrangement as claimed in claim 43, wherein the working face area is greater than about 50% of the anchor area.

46. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and further including a middle tuft of bristles arranged between the inclined bristle tufts, the middle tuft being generally aligned with the motion axis.

47. The brush arrangement as claimed in claim 46, wherein bristles of the middle tuft have distal free ends that protrude beyond the free ends of the surrounding bristle tufts.

48. The brush arrangement as claimed in claim 46, wherein the tuft distal ends collectively form a convex working face which is generally conical or pyramidal or stepped.

49. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and wherein the bristles radially more adjacent the motion axis are of greater hardness than the bristles which are radially more remote from the motion axis.

50. The brush arrangement as claimed in claim 49, wherein the bristles more adjacent the motion axis have hardness determined by a bristle strength of 7±2 mil.

51. The brush arrangement as claimed in claim 50, wherein the bristles more remote from the motion axis have hardness determined by a bristle strength of 6±2 mil.

52. The brush arrangement as claimed in claim 49, wherein the bristles more remote from the motion axis have hardness determined by a bristle strength of 6±2 mil.

53. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and wherein the tuft distal ends form a substantially planar working face.

54. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and wherein the tuft distal ends collectively form a substantially planar working face.

55. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom and a median axis extending between the proximal and distal ends, each said bristle tuft comprising a plurality of filaments arranged on opposite sides of the median axis, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and wherein the bristle carrier defines hole mounts for receiving bristle tufts, and that the bristle tuft proximal ends are secured in the bristle carrier holes using anchor wire tufting.

56. A brush arrangement for use in a toothbrush having a drive mechanism for causing movement of the brush arrangement relative to a motion axis of the brush arrangement for cleaning teeth in an oral cavity of a user, said brush arrangement comprising a bristle carrier and a plurality of upstanding bristle tufts, each bristle tuft having a proximal end secured to the bristle carrier and a distal free end remote therefrom and a median axis extending between the proximal and distal ends, each said bristle tuft comprising a plurality of filaments arranged on opposite sides of the median axis, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, and wherein the bristle tuft proximal ends are secured in the bristle carrier by injection molding.

57. A brush arrangement for use in a toothbrush having a drive mechanism for causing movement of the brush arrangement relative to a motion axis of the brush arrangement for cleaning teeth in an oral cavity of a user in combination with a brush support section defining a cavity therein, said brush arrangement comprising a bristle carrier and a plurality of upstanding bristle tufts, each bristle tuft having, a proximal end secured to the bristle carrier and a distal free end remote therefrom, wherein the bristle tufts are disposed in a spaced relationship to the motion axis and inclined in the direction of the motion axis so that their distal ends are arranged within an imaginary boundary circumferentially enclosing the tufts adjacent the free ends, said boundary having in a projection onto a plane transverse the motion axis a major dimension less than a lateral distance between outside edges of two adjacent teeth, whereby the plurality of tuft distal ends are insertable into a region between said lateral distance between adjacent teeth during a cleaning operation, said bristle carrier of the brush arrangement being rotationally disposed on said brush support section, said brush support section comprising a shaft rotationally disposed within said brush support section and adapted to be pushed into coupling relationship with and driven in rotation by a drive shaft extending from a handle of the toothbrush, and said shaft of said brush support section extending generally transverse to the motion axis of the bristle carrier and being in driving connection with said bristle carrier of the brush arrangement for causing movement of the brush arrangement relative the motion axis, the combination brush support section with brush arrangement being removably attachable to the toothbrush.

58. The brush arrangement and brush support section combination as claimed in claim 57, further in combination with the handle of the toothbrush.

59. An interproximal brush arrangement for use in a toothbrush having a drive mechanism for causing movement of the brush arrangement relative to a motion axis of the brush arrangement for cleaning teeth in an oral cavity of a user, said brush arrangement comprising a substantially planar bristle carrier, and a plurality of upstanding bristle tufts, each bristle tuft comprising a plurality of plastic bristles and dimensioned to be received within the oral cavity of a human user, each bristle tuft having a proximal end secured to the bristle carrier and a distal free end remote therefrom, wherein, at the proximal ends, centers of the bristle tufts are spaced from one another, wherein the bristle tufts are disposed in a spaced relationship to the motion axis and inclined in the direction of the motion axis.

60. The interproximal brush as claimed in claim 59, wherein the substantially planar carrier is disc-shaped.

61. The interproximal brush as claimed in claim 59, wherein the tufts have respective median axes intersecting the motion axis.

62. The interproximal brush arrangement as claimed in claim 59, wherein the distal ends are arranged within an imaginary boundary circumferentially enclosing the tufts adjacent the free ends, said boundary having in a projection onto a plane transverse the motion axis a major dimension less than a lateral distance between outside edges of two adjacent teeth.

63. The interproximal brush arrangement as claimed in claim 59, wherein the tuft distal ends form a working face having an area bounded by an imaginary distal envelope enclosing the distal ends, wherein an anchor area along the bristle carrier is bounded by a base envelope enclosing the bristle tufts near their proximal ends, and wherein the working face area is less than the anchor area.

64. The interproximal brush arrangement as claimed in claim 59, wherein the tuft distal ends form a working face having an area bounded by an imaginary distal envelope enclosing the distal ends, the working face area being between about 3 mm$^2$ and about 8 mm$^2$.

65. The interproximal brush arrangement as claimed in claim 59, wherein the bristle carrier defines hole mounts for receiving bristle tufts, and that the bristle tuft proximal ends are secured in the bristle carrier holes using anchor wire tufting.

66. The interproximal brush arrangement as claimed in claim 65, wherein the bristle tuft proximal ends are secured embedded in a front face of the bristle carrier.

67. The interproximal brush arrangement as claimed in claim 59, wherein each said tuft of bristles has its proximal end mounted in respective separate apertures in the bristle carrier.

68. The interproximal brush arrangement as claimed in claim 59, wherein each said tuft of bristles has a median axis extending between the proximal and distal ends, each said bristle tuft comprising a plurality of filaments arranged on opposite sides of the median axis.

69. An interproximal brush arrangement for use in a toothbrush having a drive mechanism for causing movement of the brush arrangement relative to a motion axis of the brush arrangement for cleaning teeth in an oral cavity of a user, said brush arrangement comprising a bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis, wherein the bristle carrier forms a radially outermost surface of the brush arrangement.

70. The interproximal brush arrangement as claimed in claim 69, wherein the bristle carrier is substantially planar.

71. An interproximal brush arrangement for use in a toothbrush having a drive mechanism for causing movement of the brush arrangement relative to a motion axis of the brush arrangement for cleaning teeth in an oral cavity of a user, said brush arrangement comprising a bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis, further including brush supporting structure supporting the motion axis of the brush arrangement, the brush arrangement being movable relative the supporting structure, and the bristle tuft distal ends extending substantially further outward, in a direction extending from the bristle carrier towards the distal ends, than portions of the brush supporting structure.

72. The interproximal brush arrangement as claimed in claim 71, wherein the bristle carrier is substantially planar.

73. An interproximal brush arrangement for use in a toothbrush having a drive mechanism for causing movement of the brush arrangement relative to a motion axis of the brush arrangement for cleaning teeth in an oral cavity of a user, said brush arrangement comprising a bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis, wherein the free ends of bristles radially more adjacent the motion axis protrude beyond the free ends of bristles which are radially more remote from the motion axis.

74. The interproximal brush arrangement as claimed in claim 73, wherein the bristle carrier is substantially planar.

75. An interproximal brush arrangement for use in a toothbrush having a drive mechanism for causing movement of the brush arrangement relative to a motion axis of the brush arrangement for cleaning teeth in an oral cavity of a user, said brush arrangement comprising a bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis, and further including a middle tuft of bristles arranged between the inclined bristle tufts, the middle tuft being generally aligned with the motion axis.

76. The interproximal brush arrangement as claimed in claim 75, wherein bristles of the middle tuft have distal free ends that protrude beyond the free ends of the surrounding bristle tufts.

77. The interproximal brush arrangement as claimed in claim 75, wherein the bristle carrier is substantially planar.

78. An interproximal brush arrangement for use in a toothbrush having a drive mechanism for causing movement of the brush arrangement relative to a motion axis of the brush arrangement for cleaning teeth in an oral cavity of a user, said brush arrangement comprising a bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis, wherein the bristles radially more adjacent the motion axis are of greater hardness than the bristles which are radially more remote from the motion axis.

79. The interproximal brush arrangement as claimed in claim 78, wherein the bristle carrier is substantially planar.

80. An interproximal brush arrangement in combination with a toothbrush having an electric drive mechanism for moving the brush arrangement relative to a motion axis of the brush arrangement for cleaning teeth in an oral cavity of a user, said brush arrangement comprising a substantially planar bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis.

81. An interproximal brush arrangement for use in a toothbrush having a drive mechanism for causing movement of the brush arrangement relative to a motion axis of the brush arrangement for cleaning teeth in an oral cavity of a user, said brush arrangement comprising a substantially planar bristle carrier, and a plurality of upstanding bristle tufts, each bristle tuft having a proximal end secured to the bristle carrier and a distal free end remote therefrom, wherein the bristle tufts are disposed in a spaced relationship to the motion axis and inclined in the direction of the motion axis, said brush arrangement in combination with a brush support section having a shaft adapted to be driven in rotation by the toothbrush and being in driving connection with the brush arrangement for causing movement of the brush arrangement relative the motion axis, the combination brush support section with the brush arrangement being removably attachable to the toothbrush.

* * * * *

UNITED STATES PATENT AND TRADEMARK OFFICE
CERTIFICATE OF CORRECTION

PATENT NO.     : 6,363,565 B1
DATED          : April 2, 2002
INVENTOR(S)    : Paffrath It is certified that error appears in the above-identified patent and that said Letters Patent is hereby corrected as shown below:

<u>Title page,</u>
Item [*] Notice, delete the phrase "by 0 days" and insert -- by 25 days --

Signed and Sealed this

Thirtieth Day of March, 2004

JON W. DUDAS
*Acting Director of the United States Patent and Trademark Office*